(12) United States Patent
Wolters et al.

(10) Patent No.: US 9,358,738 B2
(45) Date of Patent: Jun. 7, 2016

(54) ASEPTIC BLOW, FILL AND SEAL METHODS OF FABRICATING TEST SAMPLE CONTAINERS AND ASSOCIATED SYSTEMS AND CONTAINERS

(71) Applicant: bioMèrieux, Inc., Durham, NC (US)

(72) Inventors: Weihua Sonya Wolters, Raleigh, NC (US); Brian Christopher Riley, Holly Springs, NC (US); Stanley Michael Philipak, Augusta, MO (US)

(73) Assignee: bioMerieux, Inc., Durham, NC (US)

( * ) Notice: Subject to any disclaimer, the term of this patent is extended or adjusted under 35 U.S.C. 154(b) by 553 days.

(21) Appl. No.: 13/790,244

(22) Filed: Mar. 8, 2013

(65) Prior Publication Data

US 2014/0120606 A1    May 1, 2014

Related U.S. Application Data

(60) Provisional application No. 61/720,531, filed on Oct. 31, 2012.

(51) Int. Cl.
*B29C 49/46* (2006.01)
*B29C 49/20* (2006.01)
(Continued)

(52) U.S. Cl.
CPC .............. *B29D 22/003* (2013.01); *B29C 49/04* (2013.01); *B29C 49/06* (2013.01); *B29C 49/20* (2013.01); *B29C 49/46* (2013.01); *B29C 49/78* (2013.01); *B29C 2049/027* (2013.01);
(Continued)

(58) Field of Classification Search
CPC  B29C 49/78; B29C 2049/2021; B29C 49/20; B29C 49/46; B29C 2049/027; B29C 2049/2008; B29C 2049/4635; B29C 2049/4679; B29C 2049/4697
See application file for complete search history.

(56) References Cited

U.S. PATENT DOCUMENTS 4,425,090 A * 1/1984 Hansen ............... B29C 49/4817
                                                              264/511
4,528,235 A    7/1985 Sacks et al.
(Continued)

FOREIGN PATENT DOCUMENTS

WO    WO93/04118    3/1993
WO    WO94/26874    11/1994
(Continued)

OTHER PUBLICATIONS

Harris, "Controls for Blow Molding" pp. 169, 170, 182 from Rosato et al, Blow Molding Handbook, 1989, Oxford University Press.*
(Continued)

*Primary Examiner* — Robert B Davis
(74) *Attorney, Agent, or Firm* — Myers Bigel & Sibley, P.A.

(57) ABSTRACT

Methods of fabricating a culture container include: (a) forming a parison; (b) introducing flowable (e.g. colorimetric) sensor material into the parison; (c) blow molding the parison into a container body; and (d) curing the sensor material so that it attaches to an inner surface of the container body. The methods can also include adding sterile growth media into the container and sealing the container shut with an elastomeric stopper and crimped seal/cap. The process can be aseptic so that autoclaving the container is not required.

19 Claims, 6 Drawing Sheets

(51) Int. Cl.
*B29D 22/00* (2006.01)
*B29C 49/04* (2006.01)
*B29C 49/06* (2006.01)
*B29C 49/78* (2006.01)
*C12M 1/24* (2006.01)
*B29C 49/02* (2006.01)

(52) U.S. Cl.
CPC .............. *B29C 2049/2008* (2013.01); *B29C 2049/4635* (2013.01); *B29C 2049/4679* (2013.01); *B29C 2049/4697* (2013.01); *C12M 23/08* (2013.01)

(56) References Cited

U.S. PATENT DOCUMENTS

| | | | |
|---|---|---|---|
| 4,536,425 A | 8/1985 | Hekal | |
| 4,584,823 A | 4/1986 | Nagel | |
| 4,827,944 A | 5/1989 | Nugent | |
| 4,911,218 A | 3/1990 | Patitsas | |
| 4,945,060 A | 7/1990 | Turner et al. | |
| 4,960,639 A | 10/1990 | Oda et al. | |
| 4,983,432 A | 1/1991 | Bissot | |
| 4,995,519 A | 2/1991 | Rose et al. | |
| 5,000,804 A | 3/1991 | Nugent | |
| 5,049,609 A | 9/1991 | Patitsas | |
| 5,090,581 A | 2/1992 | Rose et al. | |
| 5,091,467 A | 2/1992 | Beers | |
| 5,094,955 A | 3/1992 | Calandra et al. | |
| 5,162,229 A | 11/1992 | Thorpe et al. | |
| 5,164,796 A | 11/1992 | Di Guiseppi et al. | |
| 5,217,876 A | 6/1993 | Turner et al. | |
| 5,356,052 A | 10/1994 | Poynter | |
| 5,472,753 A | 12/1995 | Farha | |
| 5,770,394 A | 6/1998 | Berndt | |
| 5,795,773 A | 8/1998 | Read et al. | |
| 5,856,175 A | 1/1999 | Thorpe et al. | |
| 5,860,329 A | 1/1999 | Day | |
| 6,123,211 A | 9/2000 | Rashid et al. | |
| 6,383,166 B1 | 5/2002 | Farris | |
| 6,709,857 B2 | 3/2004 | Bachur, Jr. | |
| 6,860,405 B1 | 3/2005 | Poynter | |
| 7,028,862 B2 | 4/2006 | Poynter | |
| 7,078,453 B1 | 7/2006 | Feeney et al. | |
| 7,119,138 B1 | 10/2006 | Feeney et al. | |
| 7,211,430 B2 | 5/2007 | Schwarz et al. | |
| 7,473,729 B2 | 1/2009 | Feeney et al. | |
| 7,803,305 B2 | 9/2010 | Ahern et al. | |
| 7,985,188 B2 | 7/2011 | Felts et al. | |
| 8,144,199 B2 | 3/2012 | Takenaka et al. | |
| 2006/0110615 A1 | 5/2006 | Karim et al. | |
| 2007/0213446 A1 | 9/2007 | Feeney et al. | |
| 2008/0014429 A1 | 1/2008 | Su et al. | |
| 2008/0131707 A1 | 6/2008 | Feeney et al. | |
| 2009/0285722 A1 | 11/2009 | Soskey et al. | |
| 2010/0068755 A1 | 3/2010 | Walsh et al. | |
| 2011/0081714 A1 | 4/2011 | Wilson et al. | |
| 2011/0081715 A1 | 4/2011 | Robinson et al. | |
| 2011/0124028 A1 | 5/2011 | Robinson et al. | |
| 2011/0133370 A1* | 6/2011 | Engelhard | B29C 49/42 264/535 |
| 2011/0186537 A1 | 8/2011 | Rodriguez San Juan et al. | |
| 2011/0252899 A1 | 10/2011 | Felts et al. | |
| 2012/0123345 A1 | 5/2012 | Felts et al. | |

FOREIGN PATENT DOCUMENTS

| | | | |
|---|---|---|---|
| WO | WO 2010137015 A2 * | 12/2010 | .......... B05B 13/0618 |
| WO | WO2011/014429 | 2/2011 | |
| WO | WO2011/016838 | 2/2011 | |
| WO | WO2011/041471 | 4/2011 | |

OTHER PUBLICATIONS

Blow molding, Packaging technology, http://packaging-technology.org/35-blow-molding.html, Jan. 31, 2012, 26 pages, printed from the internet Sep. 6, 2012.

Guidance for Industry, Sterile Drug Products Produced by Aseptic Processing—Current Good Manufacturing Practice, Pharmaceutical CGMPs, U.S. Department of Health and Human Services, Food and Drug Administration, Center for Drug Evaluation and Research (CDER), Center for Biologics Evaluation and Research (CBER), Office of Regulatory Affairs (ORA), Sep. 2004, 19 pages.

* cited by examiner

ASEPTIC BLOW, FILL AND SEAL METHODS OF FABRICATING TEST SAMPLE CONTAINERS AND ASSOCIATED SYSTEMS AND CONTAINERS

RELATED APPLICATIONS

This application claims the benefit of and priority to U.S. Provisional Application Ser. No. 61/720,531, filed Oct. 31, 2012, the contents of which are hereby incorporated by reference as if recited in full herein.

FIELD OF THE INVENTION

This invention relates to methods for fabricating containers that are particularly suitable for culturing biosamples.

BACKGROUND OF THE INVENTION

Bottles for collection or culturing of blood and other biological samples are known in the art. See, e.g., U.S. Pat. Nos. 4,945,060; 5,094,955; 5,860,329; 4,827,944; 5,000,804; 7,211,430 and U.S. Patent Application Publication 2005/0037165.

Sample culture bottles or containers typically contain a headspace gas composition to facilitate the recovery of organisms. The blood culture container is made of a suitable gas-impermeable material to ensure that the integrity of the gas composition in the headspace of the bottle is maintained throughout the shelf life of the bottle. For typical analysis, the container should ideally remain visually optically transmissive, typically transparent, through its life to allow for one or more of (i) manual or electronic observation of the contents of the container, (ii) measuring fill level when using the container, (iii) visual observation of contents after culturing or growth, and (iv) a reading of an internal sensor in the container that detects microbial growth.

Several types of blood culture bottles have been used that limit gas diffusion into or out of the bottle. One type is a glass vial with an elastomeric seal. The glass vial itself provides the gas barrier. However, if a glass vial is dropped it may break, exposing the user to glass shards and, potentially, biologically hazardous materials. Furthermore, the nature of glass manufacturing can leave undetectable micro-cracks in the glass, which under the pressure of microbial growth in the vial can lead to bottle rupturing, and, again, exposure of the user to biohazardous materials.

A second type of blood culture bottle is a multi-layer plastic vial. See, e.g., U.S. Pat. No. 6,123,211 and U.S. Patent Publication 2005/0037165. The multi-layer plastic vial is fabricated from two plastic materials that each serve different functions. For example, the interior and exterior layers of the vials can be produced from polycarbonate, which offers the strength and rigidity required for product use. Likewise, polycarbonate can withstand higher temperatures required for autoclave of the product during manufacture and remains transparent. However, the polycarbonate does not provide a sufficient gas barrier. The middle material layer can be fabricated from nylon, which provides the gas barrier required for the product. The nylon, by itself, does not have the necessary rigidity and strength to withstand the autoclave temperatures required during the manufacture of blood culture bottles, since it would not remain transparent if exposed to moisture or autoclaved. The multilayer plastic vial offers advantages over the glass vials. However, multi-layer plastic vials are produced with relatively complex manufacturing methods and the vials are consequently relatively expensive.

More recently, single layer plastic bottles have been proposed which employs an autoclave or bottle sterilization process to provide the necessary cleanliness/sterility. See, e.g., U.S. Patent Publication No. 2011/0081714, the contents of which are incorporated by reference as if recited in full herein.

Despite the above, there remains a need for cost-effective test sample containers and fabrication methods.

SUMMARY OF EMBODIMENTS OF THE INVENTION

Embodiments of the invention employ aseptic blow, fill and seal fabrication operations that do not require post-formation autoclaving for sterilization.

Some embodiments of the invention are directed to aseptic methods of fabricating a culture container. The methods include: (a) forming a parison; (b) introducing flowable sterile material into the parison; (c) blow molding the parison into a container body, before, during or after the introducing step; and (d) sealing the top of the container to maintain an inner sterile environment.

In some embodiments, the parison is formed, sensor material is introduced, the parison is blow molded into the container body, then a curing agent can be introduced into blow-molded container body before sterile growth media is added thereto and a sealing step performed.

The parison can have a temperature that is between about 25 degrees C. to about 150 degrees C. (which can vary by the parison material) when the flowable sensor material is introduced therein. The flowable sensor material can be sterile.

The forming step can include extruding the parison at a heated temperature.

The curing can be carried out by thermal energy and/or introducing a curing agent in the parison and/or blow-molded container body to thereby cause the colorimetric sensor material to adhere to the inner surface.

The colorimetric sensor material can include Liquid Emulsion Silicone ("LES").

The method can include pinching a top of the blow molded container body shut while at an elevated temperature above room temperature. The forming, introducing, curing and pinching steps can be carried out entirely using a blow-fill-seal machine in a sterile environment.

The method can also include attaching a sterile stopper to an upper portion of the container body; then inserting a needle and/or tube through the stopper while the stopper is attached to the upper portion of the container body; and applying a vacuum to an internal volume of the container body using the needle or tube.

The method can include introducing sterilized growth media into the container body before the attaching step.

The method can include introducing a defined pressurized sterile gas or gas mixture into the container body before or after the attaching step.

The method may include trimming material remnants off of an upper portion of the blow-molded container body (parison) after the attaching step and before the applying a vacuum step to expose the stopper.

The method may include applying and crimping an aluminum cap on the stopper in a sterile environment/clean room.

The method can include adding sterile microorganism growth media into the container body; automatically flowably introducing a defined pressurized sterile gas or gas mixture into the container body; then electromechanically sealably attaching an elastomeric stopper onto an upper portion of the blow-molded container body to define a post-seal filled container body; then electromechanically sealing the upper portion of the parison by melting the materials together.

The method may include electromechanically trimming an upper portion of the container body, creating a vacuum in the container body while the elastomeric stopper remains attached to the upper portion of the container body; and electromechanically adding a crimped seal cap to an upper portion of the container body over the stopper. The trimming the upper portion of the container body and the applying a the crimped seal cap can be performed in a sterile environment off the blow-fill-seal machine. The container body with the stopper and crimped seal can define a sterile internal volume ready for shipment without requiring autoclaving of the post-seal filled container body.

The parison can be formed of a polymer material that has a temperature rating that is below autoclave temperatures of an autoclave process.

The blow-molded post-seal container body can be optically transmissive.

Other embodiments are directed to systems for mass producing culture sample containers. The systems include: (a) at least one blow-mold machine with at, least one blow pin, and a plurality of blow-molding stations, each station including a mold with a mold cavity defining a container body shape; (b) at least one supply of sterile parison mold material in fluid communication with the mold stations; (c) at least one supply of sterile flowable sensor material with at least one flow path that is in fluid communication with the mold stations; and (d) at least one controller that is configured to: (i) direct the at least one blow-mold machine to form parisons from the sterile mold material; then (ii) direct the sterile flowable sensor material to flow in the flow path to the respective mold stations to enter the parisons while the parisons are hot; then (iii) direct the blow-mold machine to blow mold the parisons in the mold cavities with the sensor material therein.

The systems can include at least one supply of sterile organism growth media with at least one flow path that extends to respective mold stations; and at least one supply of elastomeric stoppers with an electromechanical delivery system that feeds a respective stopper to a respective upper portion of a container body held at one of the mold stations.

The systems may include at least one vacuum source with a corresponding flow path with a needle that is configured to travel down through the blow pin and extend through a respective stopper attached to a container body while held by the mold station to thereby pull a vacuum on an internal volume of the container body.

The systems may include a pressurized sterile gas source with a flow path that is configured to extend to a respective mold station and flow the sterile gas into a container body held by the mold station into an internal volume of the container body.

Yet other embodiments are directed to culture containers. The containers include a blow-molded container body having an inner surface with a layer of colorimetric sensor material attached thereto such that the material is in a thin layer and rises a distance up above the bottom of the container about lower inner wall surfaces. When exposed to autoclave temperatures of 137 C for 15 minutes, the container body can do one or more of (i) turn translucent or opaque; (ii) become permeable; or (iii) decrease in structural rigidity so that it is not suitable for use as visually transmissive culture container.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

Other systems and/or methods according to embodiments of the invention will be or become apparent to one with skill in the art upon review of the following drawings and detailed description. It is intended that all such additional systems, methods, and/or devices be included within this description, be within the scope of the present invention, and be protected by the accompanying claims.

BRIEF DESCRIPTION OF THE DRAWINGS

Other features of the present invention will be more readily understood from the following detailed description of exemplary embodiments thereof when read in conjunction with the accompanying drawings.

DETAILED DESCRIPTION OF EMBODIMENTS OF THE INVENTION

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise. One or more features shown and discussed with respect to one embodiment may be included in another embodiment even if not explicitly described or shown with another embodiment.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/ or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The term "about" means that the recited number or value can vary by +/−20%.

The term "sample" refers to a target material undergoing testing or analysis for content. The sample can be a food sample, an environmental sample (water, air, soil, etc.) or a biosample. The testing can be for quality control of food produced in a commercial manufacturing facility, for the EPA (the Environmental Protection Agency of the U.S. Government), for environmental toxins or hazardous materials that are man-made, intentional or not, or medical (clinical diagnostic) purposes.

The term "biosample" refers to human or animal tissue, blood, blood plasma or serum, blood fractions, joint fluid, urine, semen, saliva, feces, cerebrospinal fluid, gastric contents, vaginal secretions, tissue homogenates, bone marrow aspirates, bone homogenates, sputum or lavages, aspirates, swabs and swab rinsates, blood products (e.g., platelets, serum, plasma, white blood cell fractions, etc.), donor organ or tissue samples, and the like. In one embodiment, the biological sample tested is a blood sample, urine, cerebral spinal fluid, lavages, mucus or other solid or liquid samples for analysis which may have microbes, microorganisms, toxins and/or cellular material or other constituents of interest. Embodiments of the invention may be suitable for veterinarian use, medical human use or research for human and/or with laboratory animals. In general, any known test sample (e.g., a biological sample or specimen) can be used. For example, the test sample can be a clinical or non-clinical sample suspected of containing one or more microbial agents. Other samples that may be tested include, but not limited to, foodstuffs, beverages, pharmaceuticals, cosmetics, water (e.g., drinking water, non-potable water, and waste water), seawater ballasts, air, soil, sewage, plant material (e.g., seeds, leaves, stems, roots, flowers, and fruit) and biowarfare samples.

The term "sterile" and derivatives thereof means that the noted device or material meets or exceeds defined (e.g., food or medical) guidelines of sterility so as to be substantially (if not totally) free of contaminants for at least a defined shelf life so as to be suitable for intended uses, e.g., clinical, health, or consumer product testing for the presence of toxins, microbes, microorganisms or other target constituents in a sample undergoing analysis. The sample can undergo analysis while held in the container. The sample may be transferred after transport and/or culturing in the container for analysis.

The term "aseptic" is used interchangeably with the word "sterile". In some embodiments, the aseptic processing or fabrication complies with GMP (Good Manufacturing Practice) industry guidelines such as those associated with Guidance for Industry—Sterile Drug Products Produced by Aseptic Processing—Current Good Manufacturing Practice, U.S. Department of Health and Human Services Food and Drug Administration, September 2004. The term "sterile environment" refers to an environment that complies with his GMP and can be defined using a suitable clean room.

Embodiments of the present invention can be used in any situation where clean room conditions are maintained for the aseptic blow-fill-seal machine and/or for post blow-fill-seal assembly steps such as trim, vacuum and crimp seal or trim and crimp seal after a vacuum has been applied while a container is held by the blow-fill-seal machine. In some embodiments, the clean room can comply with the conditions of a class 1, class 10, class 100, class 1000, class 10,000, or class 100,000 clean room as set forth by the U.S. Federal Standard 209b for clean room classification. See, Federal Standard No. 209B 1992, "Clean Room and Work Station Requirements, Controlled Environment," dated Apr. 24, 1973, which is hereby incorporated by reference in its entirety.

The term "parison" refers to a preform of material that is subsequently blown into a shape defined by an enclosed mold using pressurized gas using conventional blow molding processes (typically extrusion-based methods) as is well known to those of skill in the art.

The term "automatic" means that the operation can be carried out using automated electromechanical equipment, rather than with manual labor.

Figures 1, 2:
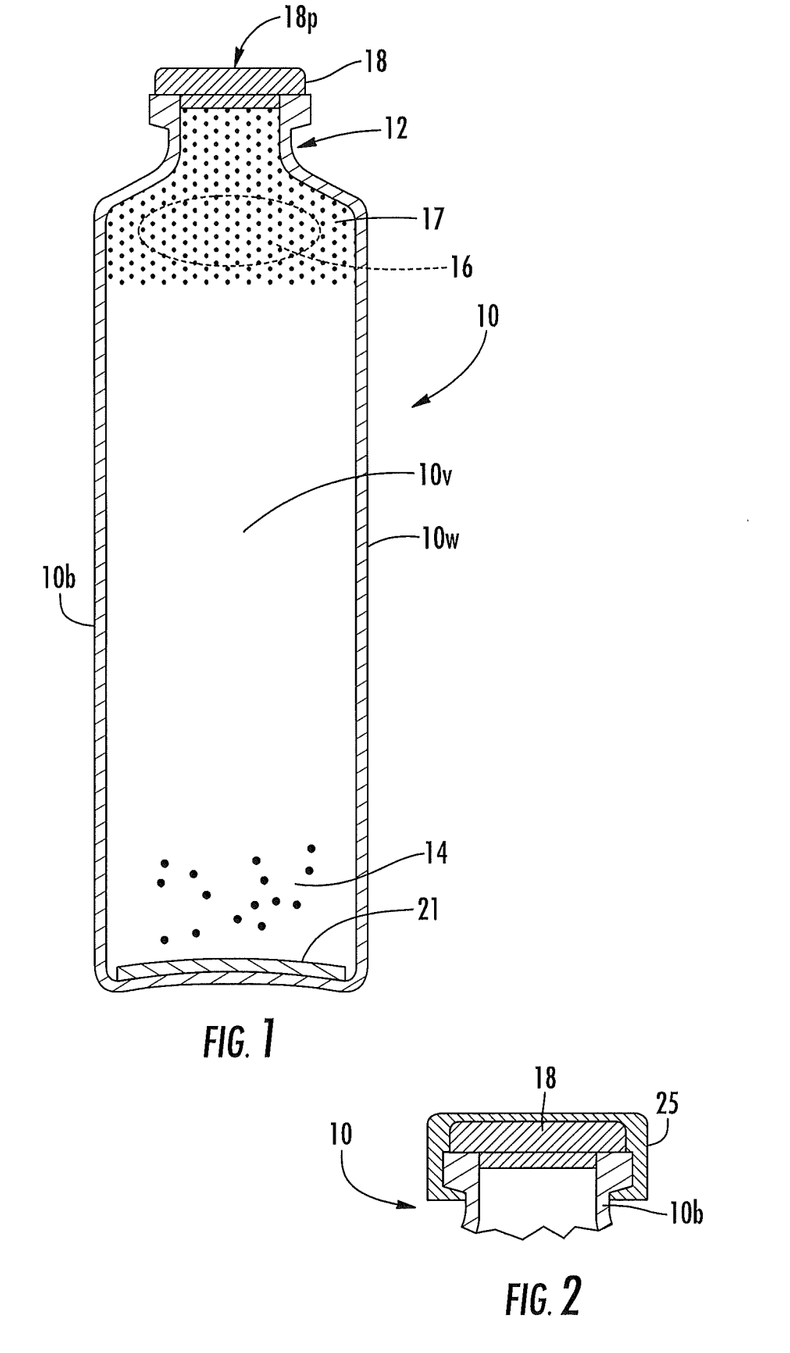
FIG. 1 is a sectional view of an exemplary culture container according to embodiments of the present invention.
FIG. 2 is a partial sectional view of an upper portion of an exemplary culture container according to embodiments of the present invention.

Turning now to the figures, FIG. 1 illustrates an exemplary sample culture container 10. The containers 10 are typically elongated containers with an internal volume 10v and an outer wall 10w having an outermost width dimension (W) being less than a height dimension (H). In some embodiments, the height (H) is greater than twice the width (W) H>2 W. In some embodiments, the containers 10 have tubular bodies with maximum outer diameters between about 1-2 inches and heights of between about 2-5 inches. In some particular embodiments, the containers 10 have an outer diameter of about 1.36 inches (34.6 mm) and a height that is about 4.68 inches (119 mm).

The container 10 can have a shape in the form of a standard culture bottle (e.g., a blood culture bottle). However, the description of a culture bottle (e.g., a blood culture bottle) is offered by way of example and not limitation. The container 10 may include a bar code label (not shown) for automated reading of patient data and/or test parameters of the content of the container 10. In some embodiments, the top portion of the container 10 can include a narrow portion or neck 12. The container 10 may also include an elastomeric stopper 18 optionally having a self-(re)sealing pierceable material and/or septum 18p.

The container 10 can have a headspace 16 that can accommodate a target (non-air) gas or gas mixture. The gas 17 in the headspace 16 can be introduced into the container 10 during manufacture as will be discussed below. Different ml ranges and different (sterile) gases 17 for the headspace 16 can be used. Typically headspace volumes are between about 20 ml to about 100 ml. One example of headspace 16 and gas 17 is 100% oxygen gas with about 50 ml headspace. Another example is about 20% carbon dioxide and about 80% oxygen with about 30 ml headspace. Yet another example is about 100% nitrogen with about 30 ml headspace. Yet another example is about 2.5% carbon dioxide, about 42.4% nitrogen, and about 55% oxygen with about 70 ml headspace. Thus, the gases introduced into the container could be oxygen, nitrogen, carbon dioxide, helium, or combination of these gases. The gas could be introduced into the container at a vacuum such as between 3-20 inch Hg, for example, about 4.5 inch, about 8 inch, or about 17 inch Hg.

In some embodiments, a cap 25, such as an aluminum or other suitable material can be placed on the top of the container 10 over the stopper 18 as shown in FIG. 2. The cap 25 is typically crimped over the stopper 18.

In some embodiments, the container 10 may also have an internal sensor 21 (e.g., an Liquid Emulsion Silicone "LES" sensor) formed or placed in the bottom portion of the container 10 for purposes of optic (e.g., visual such as colorimetric or fluorescent) detection of the internal content, e.g., presence of microbial growth in the container 10. The container 10 can include a body with an optically transmissive material. The body 10b can have a wall 10w that is substantially transparent or sufficiently translucent at the time of testing to allow for visual detection of container content therein. A variety of sensor technologies are available in the art and may suitable. In one possible embodiment, the detection unit takes colorimetric measurements as described in the U.S. Pat. Nos. 4,945,060; 5,094,955; 5,162,229; 5,164,796; 5,217,876; 5,795,773; and 5,856,175, which are incorporated by reference as if recited in full herein. A positive container is indicated depending upon these colorimetric measurements, as explained in these patents. Alternatively, detection could also be accomplished using intrinsic fluorescence of the microorganism, and/or detection of changes in the optical scattering of the media (as disclosed, for example, in co-pending U.S. patent application Ser. No. 12/460,607, filed Jul. 22, 2009 and entitled, "Method and System for Detection and/or Characterization of a Biological Particle in a Sample") which is also incorporated by reference as if recited in full herein. In yet another embodiment, detection can be accomplished by detecting or sensing the generation of volatile organic compounds in the media or headspace of the container.

Exemplary analytical instruments for analyzing the bottles for presence of organisms include U.S. Pat. Nos. 4,945,060; 5,094,955; 6,709,857 and 5,770,394, U.S. Patent Publication 2011/0124028 and PCT Publication WO 94/26874. The contents of these documents are hereby incorporated by reference as if recited in full herein. As described in more detail in U.S. Patent Publication 2011/0124028 incorporated by reference hereinabove, an automated detection system may contain one or more work-flow stations for obtaining one or more measurements, readings, scans and/or images of a specimen container, thereby providing information, such as, container type, container lot number, container expiration date, patient information, sample type, test type, fill level, weight measurement, and the like.

The container 10 may further comprise a growth or culture medium 14 for promoting and/or enhancing microbial or microorganism growth. The use of a growth or culture media (or medium) for the cultivation of microorganisms is well known. A suitable growth or culture medium provides the proper nutritional and environmental conditions for growth of microorganisms and should contain all the nutrients required by the microorganism which is to be cultivated in the specimen container 10. After a sufficient time interval to allow amplification of microorganisms (this time interval varies from species to species), the container 10 can be tested within an automated detection system for evaluating the presence of microbial or microorganism growth. The testing may occur continuously or on a periodic basis so that the container content can be electronically determined as positive for microorganism growth as soon as possible.

The container 10 includes a body 10b that is blow molded as will be discussed further below. The body can be a molded polymeric body 10b (e.g., a thermoplastic material body) which can be made from a single layer of polymeric (plastic) material. The material used to form the container body 10b can be selected so that the container body is visually transmissive and substantially impermeable at normal environmental pressures allowing for a suitable shelf life. Unlike conventional containers, the container body 10b is not required to have the necessary characteristics to be autoclaved (e.g., withstand the high temperature, high pressure and steam of autoclaving). Examples of useful materials include, but are not limited to polycarbonate, polyolefin such as polypropylene (PP), polyethylene (PE), or cyclic olefin (COC), polyester such as polyethylene terephthalate (PET) or polyethylene napthalate (PEN), polyamide (nylon), or other well known materials in the plastics art. Amorphous plastics such as amorphous nylon exhibit high transparency and may also be suitable.

The molded polymer material can have a temperature rating that is below autoclave temperatures of an autoclave process, e.g., if exposed to autoclave temperature, the molded body may turn opaque, become unsuitably permeable, become overly soft or flexible, or otherwise undesirably degrade in a mechanical, chemical and/or optical performance parameter. The term "permeable" refers to oxygen transmission rates that are above 0.2 cc/day/atm. For polymer material that has a temperature rating that is below autoclave temperatures, the sealed containers 10 when autoclaved, can make them unsuitably permeable. To assess OTR, a sealed container can be held at test conditions of 1 atm, a relative humidity ("RH %") that is 40% and a room temperature that is 20 degrees C. The oxygen transmission rate can be determined using MOCON Oxytran 2/61 Oxygen Permeability Instrument via ASTM F-1307 or other suitable instruments and protocols.

The container body 10b may include an external film (e.g., shrink wrap film, or thermoplastic polymeric film) of a gas barrier material.

The container body 10b may be surface treated, or may include an external coating (and/or internal coating) of a gas barrier material. The coating may be applied via chemical vapor deposition, plasma treatment, flow coating, dip coating, or spray coating. The coating material may be polyurethane, epoxy, carbon, parylene, silica, polyvinyl alcohol (PVOH), polyvinylidene dichloride (PVDC) containing materials.

Figure 3:
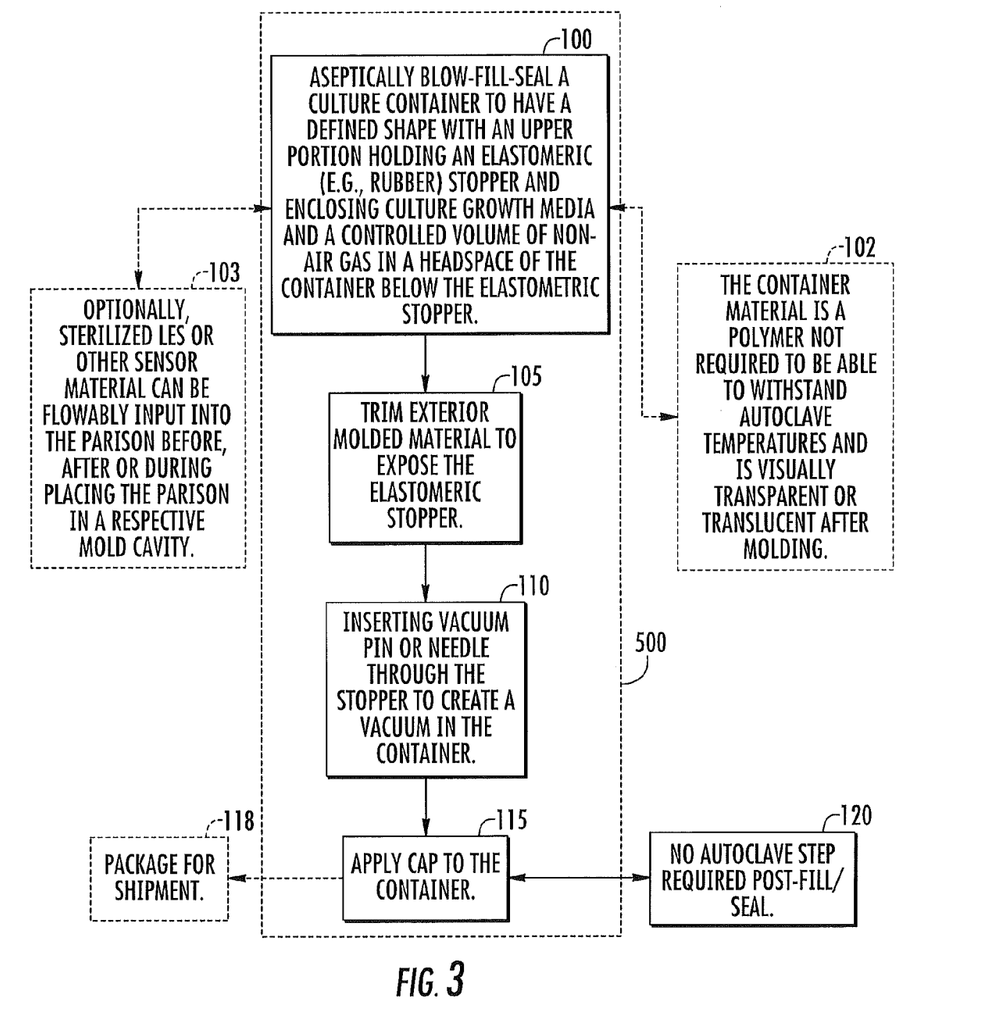
FIG. 3 is a flow chart of exemplary operations that can be carried out to fabricate culture containers according to embodiments of the present invention.

FIG. 3 illustrates exemplary operations that can be used to fabricate sample containers according to embodiments of the present invention which modifies conventional blow-fill-seal processes to produce economic culture containers. Examples of blow-fill processes are described in U.S. Pat. Nos. 4,584,823, 4,995,519, 5,090,581, 5,356,052, 6,383,166, 6,860,405 and 7,028,862, the contents of which are hereby incorporated as if recited in full herein. Some or all of the steps can be carried out in a sterile environment (in one or more clean rooms).

Generally stated, embodiments of the invention provide blow-fill-seal methods and systems where the entire fabrication process of respective culture containers is carried out aseptically on the blow-fill-seal machine 350 (FIG. 6) only including: forming the parison, introducing the LES, blow-molding the container, curing LES, introducing growth media, attaching the rubber stopper, creating the vacuum, pinching the top of the molded container body together to seal the content, then removing the pinched polymeric top of the molded container body, and attaching a crimp seal to seal the top of the container.

In other embodiments, part of the process after the stopper is applied to the top of the container body and the soft polymeric neck is pinched shut can be carried outside the machine 350 (FIG. 6) in a sterile environment 500 (which can be in the same or a different room as the machine 350).

Thus, in some embodiments, the forming the parison, introducing the LES, blow-molding the container, curing LES, introducing media, attaching the rubber stopper, and creating the vacuum can be carried out on the machine 350 (FIG. 6) and the neck of the container body can be pinched shut (before or after the vacuum is applied, while the neck is still warm). Next, in a sterile environment, which can be in the same room as the machine 350 or in a different clean room, the top of the sealed container body can be trimmed and a crimp seal (e.g., aluminum cap) applied to seal the container to be ready for use/shipment.

As yet another alternative, in some embodiments, the blow-fill-seal can include forming the parison, introducing the LES, blow-molding the container, curing LES, introducing media, and attaching the rubber stopper all while on the machine 350. Then, in a sterile environment 500 (e.g., the same room as the machine 350, FIG. 6) or in a different sterile environment or clean room, the top of the sealed container body can be trimmed, a vacuum can be created, and the container top can be crimp sealed using an aluminum cap, for example.

As shown in FIG. 3, a culture container 10 can be formed using an aseptic blow-fill-seal process so that the culture container has have a defined shape with an upper portion holding an elastomeric (e.g., rubber) stopper and enclosing culture growth media and a controlled volume of non-air gas in a headspace of the container below the elastomeric stopper (block 100). The blow-fill-seal machine 350 (FIG. 6) carrying out some or all the process steps 100 can be in a sterile environment 500. The stopper can be from a solid pre-formed (pre-sterilized) stopper or may be formed in situ in the respective mold. The container material can be a sterile polymer material that is not required to be able to withstand autoclave temperatures and is visually transparent or translucent after molding (block 102).

The exterior of an upper portion of the molded material can be trimmed to expose the elastomeric stopper (block 105). A vacuum pin or needle can be inserted through the stopper to create a vacuum in the container (block 110). A cap can be attached (crimp sealed) to the container over the stopper (block 115). No post-fill or post-seal autoclave step is required (block 120) and the container is ready to ship/use (block 118). Sterilized LES or other sensor material can be flowably input into the parison before, after or during placing the parison in a respective mold cavity (block 103). Sterile growth media can also then be introduced after the sensor material. Steps 105, 110, 115 may be carried out in a separate sterile environment or off the blow-fill-seal machine 350.

Figure 4:
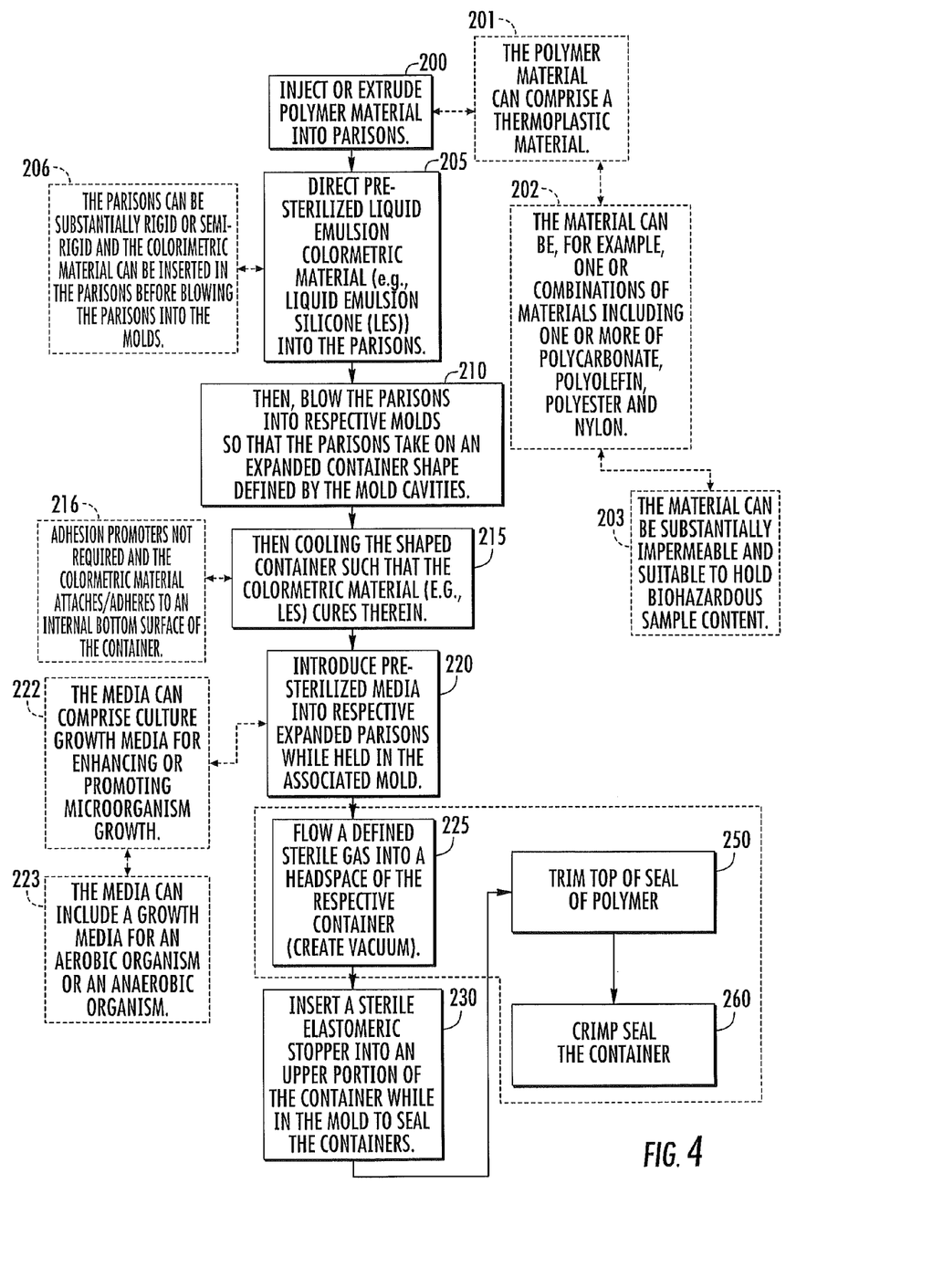
FIG. 4 is a flow chart of exemplary operations that can be carried out to fabricate culture containers according to particular embodiments of the present invention.

FIG. 4 illustrates exemplary operations of an aseptic blow-fill-seal process according to embodiments of the present invention which can produce multiple containers at a time using blow-mold equipment as is well known. Polymer material is injected or extruded into a parison (block 200). Pre-sterilized liquid emulsion colorimetric material (e.g., Liquid Emulsion Silicone (LES)) can be flowably directed into (at least a lower portion of) the hot/heated parisons (block 205). In some embodiments, the parisons can be at an elevated (above room temperature) level when the LES is introduced. In some embodiments, the parisons can have a temperature of between about 25 degrees C. to about 150 degrees C. when the liquid sensor material is flowably introduced therein. Then, the parisons can be blown into respective molds to take on the expanded shape of the respective mold cavity to form a shaped container (block 210). Then, the shaped container can be cooled such that the colorimetric material (e.g., LES) cures (solidifies) therein (block 215), typically directly attached/adhered and/or bonded to a bottom interior surface of the shaped container. In the process of blow-molding the parison, the LES can flow and cure substantially concurrently with the blow molding. Alternatively, the curing can be within a short time frame after the blow-molding. The sensor material can be attached to the internal (typically at least a lower/bottom) surface of the container without requiring the use of adhesion promoters (block 216). Pre-sterilized media can be inserted into respective expanded parisons while held in the associated mold (block 220). The media can also be inserted into the container after opening the mold. A defined sterile gas from a pressurized gas supply/source can be flowed into a headspace of a respective container (e.g., a vacuum can be created) (block 225). A sterile elastomeric stopper can be inserted into or onto an upper end portion of the container (which may optionally still be held in the mold) (block 230).

The top of the container can be pinched shut over the stopper. The pinched body of the top of the container body can be trimmed (block 250) and a crimp seal cap can be applied to the container (block 260). These steps can also be carried out on the blow-fill-seal machine or off the blow-fill-seal machine in the same or a different sterile environment 500.

The stopper can be attached before or after the sterile gas/vacuum (where used) is introduced into the container and while on the blow-fill-seal machine or off the machine but in a sterile environment (as indicated by the broken line to block 250). The stopper can be introduced while the parison is attached to the extrusion head and/or blow pin.

The polymer material can comprise a thermoplastic material (block 201). The material can be, for example, one or combinations of materials including one or more of polycarbonate, polyolefin, polyester, polyethylene and nylon (block 202). The container material can comprise one or more additives with a polymeric material. The additives can include, for example, clarifier, nucleating agent, processing agent, oxygen absorber and/or gas barrier polymers. The container material can be substantially impermeable and suitable to hold biohazard sample content (block 203) and may be visually transmissive, typically transparent.

The parisons can be substantially rigid or semi-rigid when the liquid emulsion is inserted therein (block 206). The term "semi-rigid" means that the structure can be self-supporting or that the structure can retain its shape when exposed to environmental conditions (but can flex or bend when pressure is applied thereto). The media can comprise culture growth media for enhancing or promoting microorganism growth (block 222). The media can include a growth media for an aerobic organism or an anaerobic organism (block 223).

The exterior of an upper portion of the molded material can be trimmed to expose the elastomeric stopper (FIG. 3, block 105) (either on the blow-fill-seal machine or after it has been taken off for processing in a sterile environment). A vacuum pin or needle can be inserted through the stopper to create a vacuum in the container (FIG. 3, block 110). This can be carried out before the top of the container is pinched shut and while on the blow-fill machine 350 (FIG. 6) or after the top of the container is pinched shut and off the blow-fill machine in a sterile environment. The cap can (optionally) then be attached (typically crimped sealed) to the container over the stopper (FIG. 3, block 115). No post-fill or post-seal autoclave step is required (FIG. 3, block 120) and the container is ready to ship/use.

The stoppers, sensor material and growth media (where used) can be pre-sterilized using conventional sterilization techniques, such as, for example, sterilization processes, autoclaving, electron beam (eBeam), gamma irradiation or ethylene oxide vapor hydrogen peroxide. Further, the exterior surfaces of the container 10 can be sterilized post-fill/post-seal without using autoclaving but is not required to be so processed, such as with an alcohol wipe and/or surface decontamination with VHP (vaporous hydrogen peroxide).

Figure 5A:
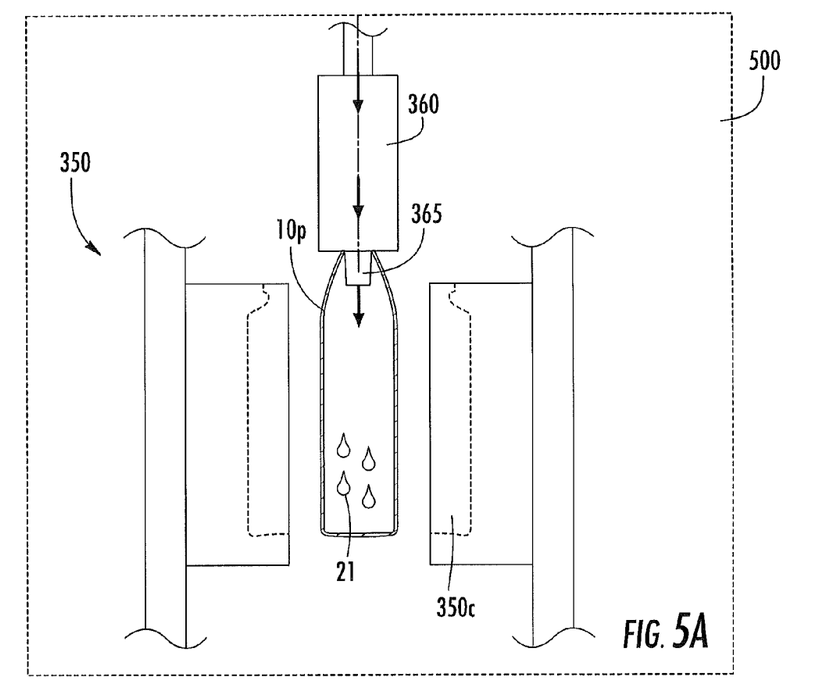
FIGS. 5A-5C are schematic illustrations of exemplary processing steps and components related to fabrication of containers using blow-mold operations according to embodiments of the present invention.
Figure 5B:
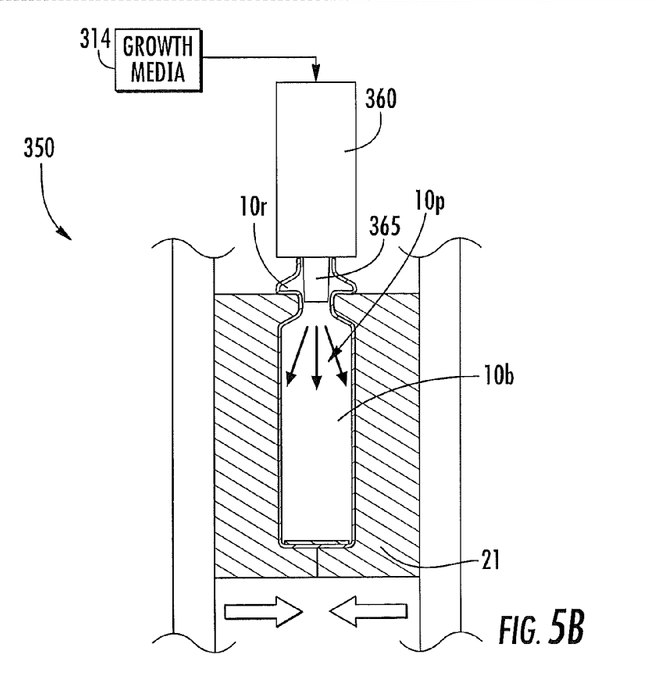
Figure 5C:
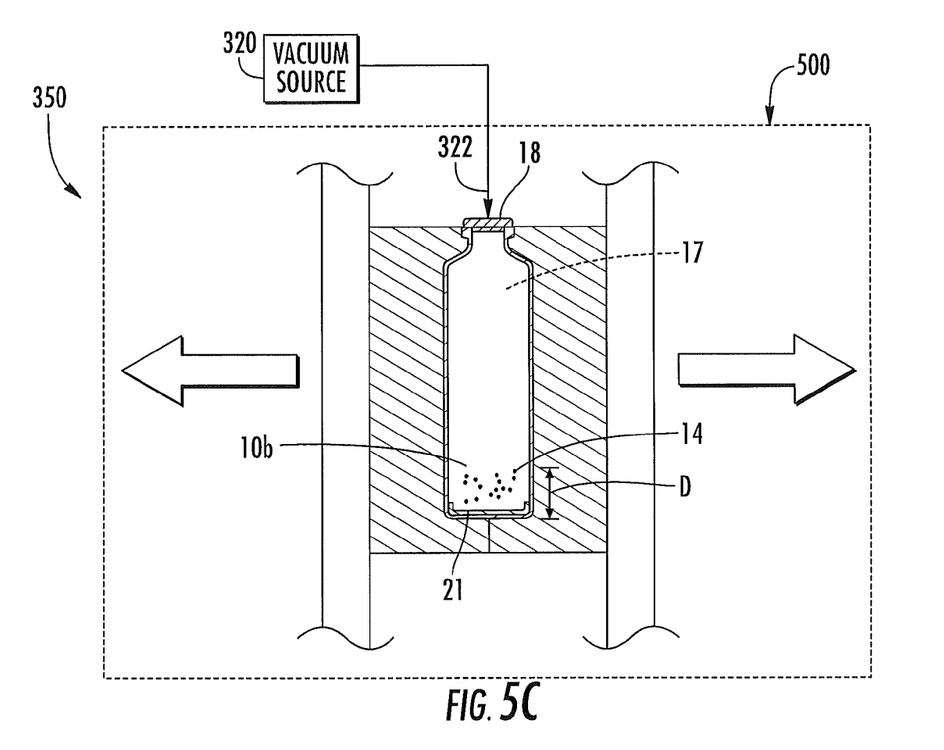

FIGS. 5A-5C illustrate exemplary operations that can be used to fabricate culture containers 10 according to embodiments of the present invention. As shown in FIG. 5A, a parison 10p is formed in a mold machine 350 for subsequent blow-molding in mold cavities 350c that form the container body shape 10b. The mold machine 350 can include an extrusion head 360 and blow pin 365. The mold machine 350 can be in a sterile environment 500 (e.g., a suitable class of clean room). As also shown in FIG. 5A, sensor material 21 is flowably introduced through the blow pin 365 into the parison 10p while the parison is hot (at a temperature above ambient), then the matable mold cavities are closed as shown in FIG. 5B. The sensor material 21 cures to attach to an inner surface of the expanded container shape. The sensor material 21 can define an internal coating that covers the bottom and may also cover at least some portions of internal sidewalls in a continuous or discontinuous manner. FIG. 5B illustrates that growth media 314 can be introduced when the mold cavities 350c are closed and after the container body is formed (blow molded/expanded). In other embodiments, the growth media 314 may be introduced after the sensor material before the blow molding step (not shown). In yet other embodiments, growth media is not required.

The remnants (or "flashing") 10r (FIG. 5B) of the parison 10p can be trimmed to allow access to the upper portion of the container body 10b before or after the stopper 18 is attached. The top of the polymeric molded container body can be pinched shut while on the blow-fill seal machine 350 (typically after the stopper 18 is attached).

FIG. 5C illustrates that the stopper 18 can be attached to the container body 10b and a vacuum source 320 may optionally engage the container body using a needle, pin or other member 322 to pull a desired vacuum. The mold 350c can be open or closed during this operation. Similarly, the pressurized sterile gas mixture/gas 17 (FIG. 1) from a gas source 317 (FIG. 6) can be introduced to the container body 10b before or after the stopper 18 is attached using the blow pin 365 or a needle or other introducer. The gas/gas mixture 17 can be introduced while the container body is held by the machine 350 while the mold cavities 350c are closed or open, typically while closed.

Although typically provided as a solid pre-formed stopper, the stopper can be formed in situ in the respective mold.

FIGS. 5B and 5C illustrate that the sensor 21 may have a different configuration from conventional culture bottles due to the blow-molding of the container body from the parison with the sensor material therein and subsequent curing. For example, the sensor material can form a thin layer that may rise a distance "D" up an inner surface of the container body, typically between about 0.1 mm to about 10 mm. The sensor material 21 can cover the inner surface of the bottom of the container for color change detection. The term "thin" refers to a layer that has a thickness that is less than a thickness of the wall of the container to which the sensor material is attached. The sensor material layer or layers can be in a thickness that is between about 0.1-50 mm, typically between about 1-10 mm.

Figure 6:
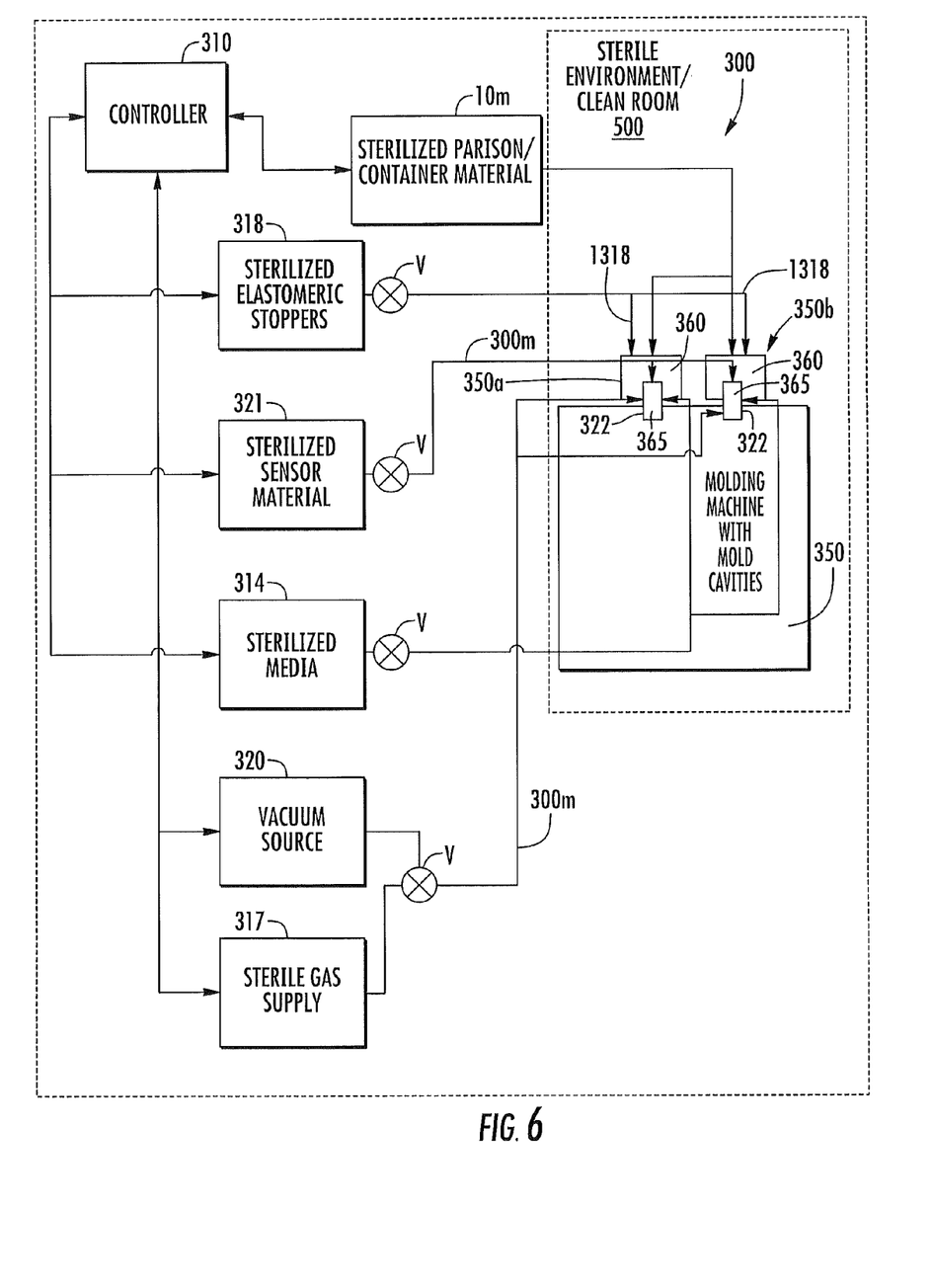
FIG. 6 is a schematic illustration of a fabrication system for mass producing culture bottles according to embodiments of the present invention.

FIG. 6 illustrates an automated system 300 for mass production of the containers 10. As shown, the system 300 includes at least one controller 310 (with at least one processor) configured to control a sequence of operations (and timing) to synchronize valves "V", flow pumps, compressors, and/or other equipment for facilitating the automated mass production/commercial process of fabricating the containers including the blow molding operations, such as the closing of respective molds against the parison after flowably introducing the sensor emulsion material into the heated/hot parison and the like. One or more sterilized manifolds 300m can connect the sterilized containers/supplies of pressurized sterile gas 317 and other material including, for example, a hopper or other supply of parison (container to be blow-molded) material 10m, a container of sterile/sterilized growth media 314, a container of sterile/sterilized LES or other sensor media 321, and the vacuum source 320 to the molding machine 350. The molding machine 350 can include at least two molding stations 350a, 350b (typically more than two) that can share or have dedicated extrusion heads 360 with associated blow pins 365 that communicate with respective mold cavities to form the shaped containers as is known to those of skill in the art.

The entire system 300 can reside in one or more sterile environments 500, but it is contemplated that at least the machine 350 is in a sterile environment with the other components having enclosed sterile feed paths/supply paths. Where some operations are carried out off the machine 350 (e.g., trim, crimp seal), a cart or other sterile closed container can be used to transport to a different sterile environment or clean room (not shown).

The flow path for some or each flowably introduced component inserted into the respective parison can include a blow pin 365 (e.g., a metal tube that allows pressurized air to enter the parison at the desired time for the blow-fill operation). Thus, the needle, pin with lumen or other vacuum introducer 322 associated with the vacuum source 320 can extend down through the pin 365 and into/through the stopper 18. Prior to this step, the stopper can be fed through the pin or inserted using a different mechanism. The stoppers can be provided using at least one supply of elastomeric stoppers with an electromechanical delivery system 1318 that can feed a respective stopper in a proper orientation to sealably attach to a respective upper portion of a container body 10b held at the mold stations 350a, 350b in the mold cavities.

The sterile gas 17 from the gas supply 317, the sensor (e.g., emulsion) material 21 from the sterilized sensor material supply 321, and the sterilized growth media 14 from the sterilized media supply 314 can be flowably introduced using the pin lumen or other flow paths.

The system 300 can be housed in a clean room 500 and may include filters that reside in a flow path that may be open to atmosphere or other components during processing. The filters may be configured to filter to a desired clean level or class, to facilitate the closed state, such as class 100,000, class 10,000, class 1000 filters or even class 100 filters. Where the cap 25 is applied in a different location off the blow-fill-seal machine 350, it can be applied in a sterile environment/clean room.

One of the exemplary uses of the containers 10 is in culturing a test sample to detect microbial growth in test sample (e.g., a blood sample) suspected of containing a microorganism therein. The method includes: (a) providing a specimen container 10 including a culture/growth medium 14 for promoting and/or enhancing growth of the microorganism; (b) introducing a test sample/specimen into the container; (c) incubating the specimen container the test sample (e.g., by placing the bottle in an incubation instrument); and (d) monitoring the specimen container for microorganism growth, either manually or automatically.

Another exemplary use of the containers 10 is in culturing a test sample to detect microbial growth in test sample (e.g., a food or environmental sample) for industrial or environmental quality or safety assessment or monitoring. The method includes: (a) providing a specimen container 10 including a culture/growth medium 14 for promoting and/or enhancing growth of the microorganism; (b) introducing a test sample/specimen into the container; (c) incubating the specimen container the test sample (e.g., by placing the bottle in an incubation instrument); and (d) monitoring the specimen container for microorganism growth, either manually or automatically.

The foregoing is illustrative of embodiments of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. An aseptic method of fabricating a culture container, comprising:
    providing at least one supply of sterile organism growth media with at least one flow path that extends to respective mold stations;
    providing at least one supply of sterile elastomeric stoppers with an electromechanical delivery system that feeds a respective stopper to a respective upper portion of a container body held at a respective mold station;
    forming parisons at the mold stations;
    introducing flowable sterile sensor material into the parisons at the mold stations;
    blow molding the parisons into a respective container body before, during or after the introducing step;
    curing the sensor material so that it attaches to an inner surface of the container body;
    sealing the container body to form a sterile container that does not require autoclaving; and
    flowing sterilized organism growth media from the provided at least one supply of sterile organism growth media after introducing the sensor material.

2. The method of claim 1, wherein the introducing flowable sensor material into the parison is carried out before the blow molding step while the container is held on a blow-fill-seal machine at respective mold stations.

3. The method of claim 1, wherein the introducing step is carried out after the blow molding step while the container body formed from the parison is at an elevated temperature and held on the blow-fill-seal machine in a sterile environment at respective mold stations.

4. The method of claim 1, wherein the sensor material is sterile colorimetric sensor material, the method further comprising pinching a top of the blow molded container body shut while at an elevated temperature above room temperature at respective mold stations, and wherein the forming, introducing, curing and pinching steps are carried out entirely using a blow-fill-seal machine in a sterile environment at respective mold stations.

5. The method of claim 1, wherein the parison has a temperature between about 25 degrees C. and about 150 degrees C. when the flowable sensor material is introduced therein.

6. The method of claim 1, wherein the curing is carried out by thermal energy and/or introducing a curing agent into the blow-molded container body to thereby cause the sensor material to adhere to the inner surface while the container body is held on a blow-fill-seal machine at respective mold stations.

7. The method of claim 1, wherein the sensor material comprises Liquid Emulsion Silicone.

8. The method of claim 1, further comprising:
    electromechanically attaching a sterile stopper from the provided supply to an upper portion of the container body; then
    electromechanically inserting a sterile needle and/or sterile tube through the stopper while the stopper is attached to the upper portion of the container body; and
    electromechanically applying a vacuum to an internal volume of the container body using the needle or tube.

9. The method of claim 8, wherein the flowing the sterilized growth media into the container body is carried Out before the attaching step.

10. The method of claim 8, further comprising applying a vacuum of a defined pressurized sterile gas or gas mixture into the container body after the attaching step.

11. The method of claim 1, wherein all of the steps are carried out while a respective container body is held by a blow-fill-seal machine in a sterile environment at a corresponding mold station.

12. The method of claim 1, further comprising:
electromechanically attaching a sterile stopper from the provided supply to a top of the container body after the growth media is added;
electromechanically sealing an upper portion of the blow-molded container body to enclose a sterile environment to carry out the sealing step;
electromechanically trimming an upper portion of the container body;
electromechanically creating a vacuum in the container body while the elastomeric stopper remains attached to the upper portion of the container body; and
electromechanically adding an external cap to an upper portion of the container body over the stopper,
wherein the flowing the sterile growth media and the electromechanically attaching the sterile stopper are carried out in a sterile environment while held on or in a blow-fill-seal machine used for the blow-molding step at the mold stations, and wherein the trimming and the adding the cap steps are carried out in a sterile environment off the blow-fill-seal machine.

13. The method of claim 1, wherein the parison can comprise polymer material that has a temperature rating that is below autoclave temperatures of an autoclave process.

14. The method of claim 12, wherein the blow-molded post-seal container body is optically transmissive.

15. A system for mass producing culture sample containers, comprising:
at least one blow-mold machine with at least one blow pin, and a plurality of blow-molding stations, each station including a mold with a mold cavity defining a container body shape;
at least one supply of sterile parison mold material in fluid communication with the mold stations;
at least one supply of sterile flowable sensor material with at least one flow path that is in fluid communication with the mold stations;
at least one supply of sterile organism growth media with at least one flow path that extends to the mold stations;
at least one supply of sterile elastomeric stoppers with at least one electromechanical delivery system that feeds a respective stopper to a respective upper portion of a container body held at the mold stations; and
at least one controller that is configured to: (i) direct the at least one blow-mold machine to form parisons from the sterile mold material; (ii) direct the sterile flowable sensor material to flow in the flow path to the respective mold stations to enter the parisons while the parisons are hot; and (iii) direct the blow-mold machine to blow mold the parisons in the mold cavities,
wherein the at least one blow-mold machine is in a sterile environment.

16. The system of claim 15, wherein the controller directs the sensor material to enter the parisons before blow molding the parisons so that the sensor material is in the parisons during the blow molding.

17. The system of claim 15, wherein the controller directs the sensor material to enter the parisons during or after the parisons are blow-molded.

18. The system of claim 15, further comprising at least one vacuum source with a corresponding flow path with a sterile needle that is configured to travel down through the blow pin and extend through a respective stopper attached to a container body while held by the mold station to thereby pull a vacuum on an internal volume of the container body.

19. The system of claim 15, further comprising a pressurized sterile gas source with a flow path that is configured to extend to a respective mold station and flow the sterile gas into a container body held by the mold station into an internal volume of the container body.

* * * * *